United States Patent
Xu et al.

(10) Patent No.: US 9,668,470 B2
(45) Date of Patent: Jun. 6, 2017

(54) METHOD FOR PRODUCING A LIQUID EMULSIFIABLE FORMULATION COMPRISING A PYRIPYROPENE PESTICIDE

(71) Applicant: BASF SE, Ludwigshafen (DE)

(72) Inventors: Wen Xu, Cary, NC (US); Ralph Paulini, Cary, NC (US); Michael Krapp, Altrip (DE); Kara Benton, Morrisville, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/760,309

(22) PCT Filed: Jan. 15, 2014

(86) PCT No.: PCT/EP2014/050650
§ 371 (c)(1),
(2) Date: Jul. 10, 2015

(87) PCT Pub. No.: WO2014/111395
PCT Pub. Date: Jul. 24, 2014

(65) Prior Publication Data
US 2015/0351382 A1 Dec. 10, 2015

Related U.S. Application Data

(60) Provisional application No. 61/753,018, filed on Jan. 16, 2013.

(51) Int. Cl.
*A01N 25/02* (2006.01)
*A01N 25/30* (2006.01)
*A01N 53/00* (2006.01)

(52) U.S. Cl.
CPC ............ *A01N 25/02* (2013.01); *A01N 25/30* (2013.01); *A01N 53/00* (2013.01)

(58) Field of Classification Search
CPC .... A01N 25/02; A01N 53/00; A01N 2300/00; A01N 25/30
See application file for complete search history.

(56) References Cited

U.S. PATENT DOCUMENTS

2010/0281584 A1* 11/2010 Horikoshi ............ C07D 493/04
800/298

FOREIGN PATENT DOCUMENTS

| EP | 1889540 | 2/2008 |
|---|---|---|
| EP | 2119361 | 11/2009 |
| EP | 2186815 | 5/2010 |
| EP | 2223599 | 9/2010 |
| WO | WO 2006129714 | 12/2006 |
| WO | WO 2012035010 | 3/2012 |
| WO | WO 2012035015 | 3/2012 |
| WO | WO 2013135604 | 9/2013 |
| WO | WO 2013135605 | 9/2013 |
| WO | WO 2013135610 | 9/2013 |

OTHER PUBLICATIONS

Narayanan, K. S. (Macro and microemulsion technology and trends. In Pesticide Formulation and Adjuvant Technology; Foy, C. L. and Pritchard, D. W. Eds.; CRC Press, Boca Raton, FL, 1996; pp. 148-164).*
International Search Report, issued in PCT/EP2014/050650, dated Mar. 4, 2014.
International Preliminary Report on Patentability, issued in PCT/EP2014/050650, dated Jul. 21, 2015.

* cited by examiner

*Primary Examiner* — Valerie Rodriguez-Garcia
(74) *Attorney, Agent, or Firm* — Brinks Gilson & Lione

(57) ABSTRACT

The present invention relates to a method for producing a liquid non-aqueous emulsifiable formulation comprising a pyripyropene pesticide of the formula (I) as defined below which is dissolved in an aromatic hydrocarbon or hydrocarbon mixture containing surfactants, which stabilize the emulsion upon dilution with water, which method comprises the steps i) and ii) as described hereinafter: i) dissolving the at least one surfactant and the compound of formula (I) in the organic solvent or solvent mixture to obtain a clear solution of the at least one surfactant and the compound of the formula (I); ii) heating the solution to a temperature of at least 40° C.

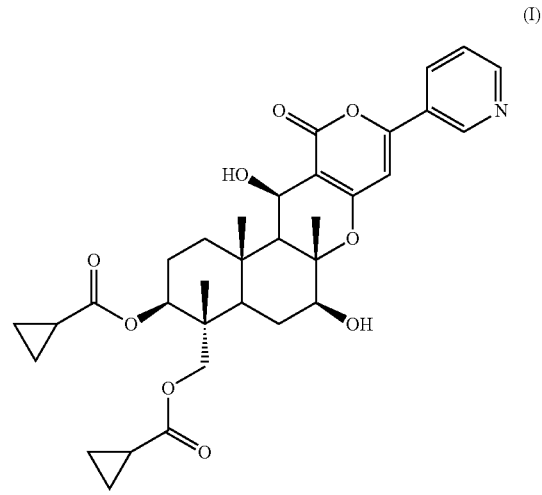

(I)

14 Claims, No Drawings

METHOD FOR PRODUCING A LIQUID EMULSIFIABLE FORMULATION COMPRISING A PYRIPYROPENE PESTICIDE

This application is a National Stage application of International Application No. PCT/EP2014/050650, filed Jan. 15, 2014, which claims the benefit of U.S. Provisional Application No. 61/753,018, filed Jan. 16, 2013.

The present invention relates to a method for producing a liquid non-aqueous emulsifiable formulation comprising a pyripyropene pesticide of the formula I as defined below which is dissolved in an organic solvent comprising an aromatic hydrocarbon or hydrocarbon mixture and containing one or more surfactants, which stabilize the emulsion upon dilution with water.

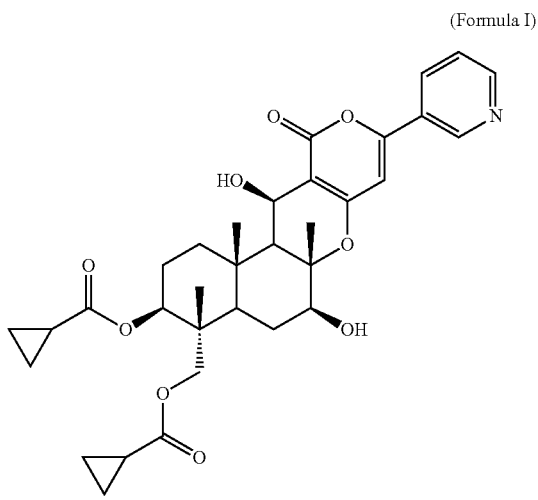

(Formula I)

The compound of formula I, hereinafter also termed pyripyropene derivative I, is known from EP 2 223 599 (compound no. 4) as exhibiting pesticidal activity against invertebrate pests, in particular against insects, and thus being useful for crop protection.

Agrochemical formulations of pyripyropene derivatives containing suitable additives are also disclosed in EP 2 223 599, EP 2 119 361 and EP 1 889 540. The pyripyropene derivative I may be prepared by the process described in WO 2006/129714 or EP 2 186 815.

Active ingredients are often formulated in the form of solutions of the active ingredient in an aromatic hydrocarbon or hydrocarbon mixture. These formulations contain one or more surfactants for stabilization of the emulsion, which is formed upon dilution of the formulation with water. Such formulations are usually termed emulsifiable formulations or emulsifiable concentrates, respectively.

One problem associated with liquid emulsifiable formulations of the pyripyropene derivative of formula I is their low physical stability upon storage. In particular, when trying to provide agricultural formulations comprising the pyripyropene derivative I solubilized in an aromatic hydrocarbon solvent, the formation of a crystalline material is observed upon storage. As the crystalline matter separates as solid material from the solution, dosage problems and clogging of the spraying apparatus may occur. Without being bound to theory, it is believed that the pyripyropene derivative I forms solvate complexes with the aromatic solvent included in the formulation.

WO 2012/035015 teaches emulsifiable formulations of the compound of the formula I, which in addition to the solvent and a conventional surfactant contain a surface active adjuvant, in particular a polyalkoxylated alcohol. The adjuvant significantly enhances the insecticidal activity of pyripyropene derivative I. However, the adjuvant may interfere with the solubilization of the pyripyropene derivative I and thus, the adjuvant may therefore further decrease physical stability of such formulations.

Earlier filed U.S. provisional patent application 61/609, 965 (published as WO 2013/356610) teaches that a certain group of non-ionic surfactants, i.e. $C_2$-$C_3$-polyalkoxylates of $C_{10}$-$C_{22}$-hydroxy fatty acid triglycerides or $C_2$-$C_3$-polyalkoxylates of $C_{10}$-$C_{22}$-fatty acid mono- or diglycerides, suppress the formation of crystalline material to a certain extent. They also found that certain ketones suppress the formation of crystalline material in liquid emulsifiable formulations of pyripyropene derivative I, which contain an aromatic hydrocarbon solvent, in particular in combination with the surfactant S. However, depending on the provenience of the pyripyropene derivative I, the stability of the obtained formulation is not always satisfactory and the use of ketones is not always possible due to regulatory constraints.

Accordingly, it is an object of the present invention to provide a method for producing stable liquid emulsifiable formulations of the pyripyropene compound of formula I. It is a particular object of the present invention to provide a method for producing stable liquid emulsifiable formulations which, besides the compound of formula I and an aromatic hydrocarbon solvent or solvent mixture, also contain an activity enhancing adjuvant. The method should yield formulations having high stability even after prolonged periods of storage and should not form crystalline material, irrespectively of the starting material used.

The inventors of the present invention found that the problems associated with the formulation of pyripyropene derivative I as an emulsifiable formulation containing aromatic solvents or solvent mixtures can be overcome by a specific method of its preparation. This specific method comprises the steps i) and ii) as described hereinafter:

i) dissolving the at least one surfactant and the compound of formula I in the organic solvent or solvent mixture to obtain a clear solution of the at least one surfactant and the compound of the formula I;

ii) heating the solution to a temperature of at least 40° C.

Accordingly, the present invention provides a method for producing an emulsifiable formulation, which formulation comprises a) the compound of formula I;
b) an organic solvent or solvent mixture having a solubility in water of not more than 10 g/l (20° C., 1 bar) and comprising at least one aromatic hydrocarbon solvent; and
c) at least one surface active substance;

characterized in that the method comprises the steps i) and ii) as described herein.

The method of the present invention has a number of advantages. The formulations obtained by the method according to the invention are homogeneous formulations which are stable for prolonged storage periods even at extreme temperatures of down to −20° C., without loosing their advantageous properties.

In the context of the present invention, the terms used generically are defined as follows:

The prefix $C_x$-$C_y$ denotes the number of possible carbon atoms in the particular case.

The term "alkyl" refers to saturated straight-chain, branched or cyclic hydrocarbon radicals having from 1 to 36 carbon atoms, e.g. methyl, ethyl, propyl, 1-methylethyl (isopropyl), butyl, 1-methylpropyl (sec-butyl), 2-methylpropyl (isobutyl), 1,1-dimethylethyl (tert-butyl), pentyl, 1-methylbutyl, 2-methylbutyl, 3-methylbutyl, 2,2-dimethylpropyl, 1-ethylpropyl, cyclopentyl, hexyl, 1-methylpentyl, n-heptyl, n-octyl, 2-ethylhexyl, n-nonyl, n-decyl, 1-methylnonyl, 2-propylheptyl, n-dodecyl, 1-methyldodecyl, n-tridecyl, n-tetradecyl, n-pentadecyl, n-hexadecyl, n-heptadecyl, n-octadecyl, n-nonadecyl, n-eicosyl, and the like.

The term "alkenyl" as used herein denotes in each case a singly unsaturated hydrocarbon radical having from 1 to 36 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-enyl, hex-2-enyl, 1-methylpent-2-enyl, hep-2-entyl, oct-4-enyl, 2-ethylhex-2-enyl, non-3-enyl, dec-4-enyl, 1-methylnon-3-enyl, 2-propylhept-3-enyl, dodec-2-enyl, 1-methyldodec-3-enyl, tridec-6-enyl, tetradec-4-enyl, pentade-2-encyl, hexadec-6-enyl, heptadec-8-enyl, octadec-2enyl, nonadec-3-enyl, and the like.

The terms "fatty acid", "fatty alcohol", "fatty amine" and "fatty amide" refer to alkanoic acids, alkanols, alkylamines or alkanoic amides having from 6 to 30, in particular from 8 to 22 carbon atoms and wherein the saturated alkyl radical may be linear or branched.

The term "$C_2$-$C_4$-alkylene" refers to saturated, divalent straight-chain or branched hydrocarbon radicals having 2, 3, or 4 carbon atoms, such as, for example, ethane-1,2-diyl, propane-1,3-diyl, propane-1,2-diyl, 2-methylpropane-1,2-diyl, butane-1,4-diyl, butane-1,3-diyl (=1-methylpropane-1,3-diyl), butane-1,2-diyl and butane-2,3-diyl.

The terms "alkoxylated", "ethoxylated", "polyoxyalkylene" or "polyoxyethylene", respectively, mean that OH-functions have been reacted with ethylene oxide or $C_2$-$C_4$-alkylene oxide to form a oligoalkylene oxide (=polyoxyalkylene) or oligoethylene oxide (=polyoxyethylene) group. The degree of alkoxylation or ethoxylation (number average of alkylene oxide or ethylene oxide repeating units) will usually be in the range from 1 to 50 and in particular from 2 to 40 more preferably from 2 to 30. Likewise, the term "alkoxylates" refers to compounds having at least one oligoalkylene oxide (=polyoxyalkylene) or oligoethylene oxide (=polyoxyethylene) group, wherein the degree of alkoxylation or ethoxylation (number average of alkylene oxide or ethylene oxide repeating units) will usually be in the range from 1 to 250 or 2 to 250, in particular from 2 to 100 or 3 to 100, more preferably from 3 to 50 or 5 to 50, especially from 3 to 30.

The term "aryl" refers to aromatic radicals including heteroaromatic radicals having 1 or 2 heteroatoms selected from the group consisting of O and N, such as, for example, phenyl, naphthyl, anthracenyl, pyridyl, pyrryl, pyrazinyl, pyrimidinyl, purinyl, indolyl, quinolyl, isoquinolyl, imidazolyl, pyrazolyl, indazolyl, furyl, benzofuryl, isobenzofuryl, morpholinyl, oxazolyl, benzoxazolyl, isoxazolyl and benzisoxazolyl.

In a first step i) of the process of the invention, the at least one surfactant and the compound of formula I are dissolved in the organic solvent or solvent mixture. Thereby a clear solution of the at least one surfactant and the compound of the formula I in the organic solvent or solvent mixture (hereinafter also termed solvent S) is obtained.

It is principally possible to perform steps i) and ii) together, i.e. to dissolve the at least one surfactant and the compound of formula I in the organic solvent or solvent mixture with heating to a temperature of at least 40° C., in particular at least 45° C., especially at least 50° C., e.g. in the range of from 40 to 90° C., in particular in the range from 45 to 85° C., especially in the range from 50 to 80° C. Preferably, dissolution of the compound of formula I in the organic solvent or solvent mixture is performed with agitation or stirring.

Frequently steps i) and ii) are performed successively, i.e. the at least one surfactant and the compound of formula I are dissolved in the organic solvent or solvent mixture at a temperature below 40° C., in particular at a temperature of at most 35° C. or at most 30° C., more particularly at a temperature in the range of from 10 to 35° C., especially in the range form 15 to 30° C., until a solution is obtained. Then the solution is heated to a temperature of at least 40° C., in particular at least 45° C., especially at least 50° C., e.g. in the range of from 40 to 90° C., in particular in the range from 45 to 85° C., especially in the range from 50 to 80° C. Preferably, dissolution of the compound of formula I in the organic solvent or solvent mixture is performed with agitation or stirring.

Preferably, the solution of the compound of formula I and the at least one surfactant in the organic solvent is heated for at least 0.5 h, in particular for at least 1 h, especially for at least 1.5 h to a temperature of at least 40° C., in particular at least 45° C., especially at least 50° C., e.g. in the range of from 40 to 90° C., in particular in the range from 45 to 85° C., especially in the range from 50 to 80° C. In particular, the solution of the compound of formula I and the at least one surfactant in the organic solvent is heated for 0.5 to 120 h, in particular for 1 to 48 h, especially for 1.5 to 24 h to a temperature of at least 40° C., in particular at least 45° C., especially at least 50° C., e.g. in the range of from 40 to 90° C., in particular in the range from 45 to 85° C., especially in the range from 50 to 80° C.

It is advantageous to dissolve the surfactant in the organic solvent S, in order to obtain a solution of the at least one surfactant in the solvent S and then to dissolve the compound of the formula I in the thus obtained solution of the at least one surfactant in the solvent S. Dissolution of the at least one surfactant in the solvent S can normally be achieved by mixing the at least one surfactant and the organic solvent or solvent mixture, preferably with agitation or stirring. Then the compound of the formula I is dissolved in the thus obtained solution of the at least one surfactant in the solvent S. Preferably, dissolution of the compound of formula I in the solution of the surfactant in the solvent S is performed with agitation or stirring. Dissolution of the compound of formula I in the solution of the at least one surfactant in the solvent S can be performed with heating to a temperature of at least 40° C., in particular at least 45° C., especially at least 50° C., e.g. in the range of from 40 to 90° C., in particular in the range from 45 to 85° C., especially in the range from 50 to 80° C. Frequently, the compound of formula I is dissolved in the solution of the at least one surfactant in the organic solvent or solvent mixture at a temperature below 40° C., in particular at a temperature of at most 35° C. or at most 30° C., more particularly at a temperature in the range of from 10 to 35° C., especially in the range form 15 to 30° C. until a solution is obtained and then the solution is heated to a temperature of at least 40° C., in particular at least 45° C., especially at least 50° C., e.g. in the range of from 40 to 90° C., in particular in the range from 45 to 85° C., especially in the range from 50 to 80° C.

As a starting material for the preparation of the solution, any crystalline or amorphous form or mixtures of different crystalline forms or mixtures of amorphous forms or crystalline forms of the pyripyropene compound of formula I can be used. In a preferred embodiment of the invention, the solution is prepared from a crystalline solvate of the compound of formula I. In particular the solvate is a crystalline solvate of the compound of formula I with a $C_1$-$C_4$-alkyl benzene, especially a solvate of the compound of formula I with toluene or ethylbenzene. These crystalline solvates of the compound of formula I can be prepared by crystallization of the compound of formula I from a solution of the compound of the formula I in a $C_1$-$C_4$-alkyl benzene containing solvent or solvent mixture, in particular from a solution of the compound of the formula I in a $C_1$-$C_4$-alkyl benzene, especially from a solution in toluene or ethylbenzene. The purity of the pyripyropene derivative I used in the method of the present invention is of minor importance. The pyripyropene derivative I will normally have a purity sufficient for its intended use as a pesticide. The purity of the pyripyropene derivative I will be generally at least 90%, in particular at least 95% or at least 97%. Purity has to be understood as the relative amount of pyripyropene derivative I in the organic solid active ingredient suspended in the slurry, except for solvents, e.g. solvents contained in the solvate.

The concentration of the pyripyropene compound of formula I in the solution is of minor importance. For practical reasons the concentration of the compound of formula I in the solution is from 0.5 to 30% by weight, in particular from 1 to 20% by weight, especially from 1 to 10% by weight, based on the total weight of the solution.

The organic solvent S used for preparing the formulation comprises at least one aromatic hydrocarbon solvent, which may be a pure aromatic hydrocarbon or a mixture of such aromatic hydrocarbons. Suitable aromatic hydrocarbons or hydrocarbon mixtures in this context are those having a melting point of below 10° C., in particular below 5° C. and a boiling point of from 100 to 310° C. (1 bar). Suitable aromatic hydrocarbons or hydrocarbon mixtures are preferably selected from mono- and polycyclic aromatics that are optionally substituted with one or more aliphatic or aralphatic substituents, in particular alkyl or arylalkyl radicals. According to a preferred embodiment of the invention the formulations comprise mixtures of those aromatic hydrocarbons which are obtained as fractions in the distillation of, in particular, mineral oil products in the abovementioned boiling point range, such as the commercially available products which are known by the trade names Solvesso® (ExxonMobil Chemical), in particular Solvesso® 100, Solvesso® 150, Solvesso® 200, Solvesso® 150 ND, Solvesso® 200 ND, Aromatic® (ExxonMobil Chemical), in particular Aromatic® 150, Aromatic® 200, Aromatic® 150 ND and Aromatic® 200 ND, Hydrosol® (DHC Solvent Chemie), in particular Hydrosol® A 200 and Hydrosol® A 230/270, Caromax® (Petrochem Carless), in particular Caromax® 20 and Caromax® 28, Aromat K (K. H. Klink Chemierohstoffe), in particular Aromat K 150, Aromat K 200, Shellsol® (Shell Chemicals), in particular Shellsol® A 100 and Shellsol® A 150, and Fin FAS-TX, in particular Fin FAS-TS 150 and Fin FAS-TX 200. Particular preference is given to Aromatic® 200 ND and Solvesso® 200 ND, in which the potential carcinogen naphthalene has been depleted. Aromatic® 200 ND and Solvesso® 200 ND both comprise mainly aromatic hydrocarbons having 10 to 14 carbons which boil in the range 240 to 300° C. and which are in particular alkylnaphthalenes. Pure aromatic hydrocarbons such as toluene, xylenes, ethylbenzene, cumene and mixtures thereof may also be used as a solvent S.

The relative amount of aromatic hydrocarbon solvent, based on the total amount of the organic solvent S is generally at least 50 vol.-%, in particular at least 80 vol.-%, especially at least 90 vol.-%, based on the total amount of the organic solvent S. In particular, the aromatic hydrocarbon solvent is the only solvent or makes up at least 95 vol.-%, especially at least 99% of the organic solvent S.

In addition to the aromatic hydrocarbon or hydrocarbon mixtures the solvent S may comprise one or more organic solvents different from aromatic hydrocarbons. Suitable solvents different from aromatic hydrocarbons will usually have a melting point of below 10° C., in particular below 5° C. and a boiling point of from 100 to 310° C. (1 bar). The amount of solvents different from aromatic hydrocarbons will generally not exceed 50% by weight, in particular 20% by weight, especially 10% by weight, based on the total amount of solvents. In a particular embodiment, the solvent S does not comprise a solvent different form the aromatic hydrocarbon solvent, which means that the amount of such solvents is less than 5% by weight, in particular less than 1% by weight, based on the total amount of solvents.

Suitable solvents, which are different from aromatic hydrocarbon solvent are principally any solvent which can be used for agricultural purposes. Suitable solvents, which are different from aromatic hydrocarbon solvent, include e.g.

ketones having from 6 to 10 carbon atoms ($C_6$-$C_{10}$-ketone) such as optionally alkoxylated aliphatic, cycloaliphatic and araliphatic ketones having 6 to 10 carbon atoms; for example, 2-hexanone, 3-hexanone, 2-heptanone, 3-heptanone, 4-heptanone, 2-octanone, 3-octanone, 4-octanone, 3-nonanone, 4-methyl-2-pentanone, 5-methyl-2-hexanone, cyclopentanone, cyclohexanone, cycloheptanone, cyclooctanone, cyclohexylcarbonylmethane, acetophenone and methoxyacetophenone;

$C_2$-$C_4$-alkylene carbonates such as ethylene carbonate (1,3-dioxolan-2-one), propylene carbonate (4-methyl-1,3-dioxolan-2-one) and 1,2-butylene carbonate (4-ethyl-1,3-dioxolan-2-one);

aliphatic and cycloaliphatic hydrocarbons such as hexanes, heptanes, octanes and cyclohexanes and mixtures thereof.

The organic solvent S is used in an amount of 20 to 80% by weight, in particular from 30 to 70% by weight, based on the total weight of the final formulation. Generally, the amount of organic solvent S comprised in the final formulation obtained by the method of the invention depends in each individual case on the amounts of the pyripyropene derivative I, the surfactant and optional further ingredients, and also their properties. The weight ratio of solvent S to the amount of the pyripyropene derivative I is usually in the range from 0.3:1 to 100:1, preferably from 1:1 to 60:1, in particular from 2:1 to 40:1, and specifically from 3:1 to 20:1. Based on the total weight of the formulation, the proportion of aromatic hydrocarbon solvent is preferably from 25 to 75% by weight, in particular from 30 to 70% by weight and specifically from 40 to 70% by weight.

The solutions prepared in step i) and thus the finally obtained formulations contain at least one surface active substance, also termed surfactant. The formulation obtained by the method of the present invention will generally contain at least one surface-active substance, which assists emulsification of the formulation upon dilution of the formulation with water. The surfactant will also stabilize the oily droplets in the thus obtained emulsion. These types of surfactants are also referred to as emulsifiers or stabilizers. The skilled worker is familiar with suitable surfactants for formulating agrochemical formulations as emulsifiable formulations, for example through McCutcheon, Detergents and Emulsifiers, Int. Ed., Ridgewood, N.Y. The surfactants used for emulsification/stabilization may be polymeric or nonpolymeric surfactants and may be anionic or non-ionic or mixtures thereof.

The surface-active substances included in the solution and final formulation may also contain a surface active substance which enhances the activity or bioavailability of the compound of the formula I. These types of surface active substance are called adjuvants. Suitable surface active compounds which may serve as adjuvants are known to an expert, for example from Hazen, Weed Technology, 2000, 14, 773-784 "Adjuvants-terminology, classification and chemistry". Examples are wetter-spreader adjuvants, sticker adjuvants, humectants, or penetration agents.

The total amount of surfactant contained in solution of step i) and also in the final formulation is preferably from 5 to 50% by weight, in particular from 10 to 45%, especially form 15 to 30% by weight, based on the total weight of the formulation or of the solution, respectively.

In a particular embodiment, the surface active substance comprises at least one non-ionic, surface active adjuvant as a component c.1). The amount of component c.1), if present, is generally in the range form 5 to 50% by weight, in particular from 10 to 40% by weight, and especially in the range from 15 to 30% by weight, based on the total weight of the formulation.

Amongst non-ionic, surface active adjuvants those are preferred which comprise at least one component, which carries at least one oligo- or polyalkyleneoxide moiety, in particular at least one oligo- or poly-$C_2$-$C_4$-alkyleneoxide moiety. An oligo- or poly-$C_2$-$C_4$-alkyleneoxide moiety is a radical, which has the formula O-$(AO)_k$—$R^x$, where $R^x$ is hydrogen, $C_1$-$C_{20}$-alkyl, $C_1$-$C_{20}$-alkylcarbonyl, or benzyl, in particular hydrogen, $C_1$-$C_4$-alkyl, $C_1$-$C_4$-alkylcarbonyl, k is a number from 2 to 250, in particular from 3 to 100, especially from 5 to 50 and where AO within the group $(AO)_k$ may be identical or different and is selected from alkylene oxide, in particular from $C_2$-$C_4$-alkylene oxide such as ethylene oxide, 1,2-propylene oxide, isobutylene oxide (2-methyl-1,2-propylene oxide) and 1,2-butylene oxide, in particular from ethylene oxide and mixtures of ethylene oxide with 1,2-propylene oxide. If $R^x$ is different from H, the oligo- or polyalkyleneoxide moiety is also termed "endcapped oligo- or polyalkyleneoxide moiety", respectively. Amongst the group of compounds which carry at least one poly-$C_2$-$C_4$-alkyleneoxide moiety, those are preferred wherein the poly-$C_2$-$C_4$-alkyleneoxide moiety comprising one or more ethyleneoxide moieties and optionally one ore more 1,2-propylene oxide moieties, isobutylene oxide and/or 1,2-butylene oxide moieties.

Suitable non-ionic surfactants which may be components of an adjuvant c.1) and which carry at least one polyalkylene oxide moiety, in particular at least one poly-$C_2$-$C_4$-alkylene oxide moiety, include, but are not limited to oligo- or polyalkoxylates of $C_6$-$C_{22}$-alkanols, in particular oligo- or poly-$C_2$-$C_4$-alkoxylates of $C_6$-$C_{22}$-alkanols, oligo- or polyalkoxylates of amines, in particular oligo- or poly-$C_2$-$C_4$-alkoxylates of $C_6$-$C_{22}$-alkylamines, oligo- or polyalkoxylates of amides, in particular oligo- or poly-$C_2$-$C_4$-alkoxylates of $C_6$-$C_{22}$-alkylamides, oligo- or polyalkoxylates of fatty acids and oligo- or polyalkylene oxide-modified polydimethylsiloxanes, in particular oligo- or poly-$C_2$-$C_4$-alkoxylene oxide-modified polydimethylsiloxanes.

Particular preferred non-ionic surfactants which may be components of an adjuvant c.1) and which carry at least one polyalkylene oxide moiety, in particular at least one poly-$C_2$-$C_4$-alkylene oxide moiety, are selected from the group consisting of alkoxylated aliphatic alcohols, in particular oligo- or poly-$C_2$-$C_4$-alkoxylates of $C_6$-$C_{22}$-alkanols, alkoxylated polydimethylsiloxanes, in particular oligo- or poly-$C_2$-$C_4$-alkoxylene oxide-modified polydimethylsiloxanes, and alkoxylates of fatty acids, in particular oligo- or poly-$C_2$-$C_4$-alkoxylates of $C_6$-$C_{22}$-fatty acids.

Examples of suitable non-ionic surfactants which may be a component of an adjuvant and which carry at least one poly-$C_2$-$C_4$-alkyleneoxide moiety include, but are not limited to:

terminally capped alkoxylated fatty alcohols and terminally capped alkoxylated straight-chain alcohols, commercially available, for example, in the product series Plurafac®; preference is given to ethoxylated and/or butoxylated fatty alcohols and terminally capped ethoxylated and/or butoxylated straight-chain alcohols;

tributylphenol polyglycol ethers having 10 to 15 EO units (where EO means ethylene oxide), commercially available, for example, as Sapogenat®;

oligo- or polyalkylene oxide-modified polydimethylsiloxanes, commercially available, for example, in the product series Silwet® and blends such as Sylgard® 309 from Dow Corning (containing 3-(3-hydroxypropyl)-heptamethyltrisiloxane, ethoxylated acetate (CAS 125997-17-3)>60%; allyloxy polyethylene glycol monallyl acetate (CAS 27252-87-5) 15 40% and polyethylene glycol diacetate 1-5%), Silwet® L-77 from Helena Chemical Company (containing polyalkyleneoxide modified heptamethyltrisiloxane (CAS 27306-78-1) 84%, allyloxypolyethyleneglycol methyl ether (CAS 27252-80-8) 16%), Freeway® from Loveland Products, Inc. (containing Silicone-polyether copolymer, linear alcohol ethoxylates, propylene glycol, dimethylpolysiloxane) and Kinetic® Molecular Zippering Action (Polyalkyleneoxide modified polydimethylsiloxane, Polyoxyethylene-polyoxypropylene copolymer (CAS 9003-11-6), Polyoxypropylene oleate butyl ether (CAS 37281-78-0));

branched alkanol alkoxylates of the formula $C_tH_{2t+5}$(—$CH_2$—$CH_2$—O—$)_u$-H, in which t represents numbers from 11 to 13.5 and u represents numbers from 6 to 25 (preferably from 8 to 12) and t and u are average values, commercially available, for example, in the product series Lutensol®;

polyalkoxylated triglycerides, in particular polyethoxylated triglycerides where the triglyceride is preferably of vegetable origin, commercially available, for example, in the product series Crovol®;

alkoxylated fatty amines, commercially available, for example, in the product series Armoblen®;

PEG-10 coconut alcohol, commercially available, for example, in the product series Genapol®;

Brij® 92, comprising oleyl alcohol ethoxylate with an average of 2 moles of ethoxylate;

Turbocharge®, comprising proprietary blend of oils and short chain ethoxylates;

Merge®, comprising proprietary blend of oils and short chain ethoxylates;

Dash®, comprising proprietary blend of oils and short chain ethoxylates;

Ethomeen® S12, comprising short chain ethoxylated fatty amine;

Alkanol alkoxylates of the formula A as defined below.

For the purpose of being an adjuvant, the nonionic surfactant may be used as such or as a solution in a suitable solvent, e.g. a non-polar solvent. Suitable non-polar solvents include the mineral oils, vegetable oils, esters of vegetable oils, fatty acid esters with 10 to 20 carbon atoms in the acid moiety and 1 to 10 carbon atoms in the alcohol moiety, esters of saturated or unsaturated dicarboxylic acids with 4 to 12 carbon atoms in the acid moiety and 1 to 8 carbon atoms in each alcohol moiety, esters of aromatic dicarboxylic acids with 1 to 8 carbon atoms in the alcohol moiety and polydimethylsiloxanes. The amount of non-ionic surfactants in these solutions may vary from 10 to 80%, in particular from 15 to 50% by weight.

Examples of adjuvants are listed in Table 1 based on their brand name including their main functional components.

TABLE 1

Adjuvants listed by brand name

| Brand Name | Adjuvant type | Main functional components |
| --- | --- | --- |
| AD-SPRAY ® 80 | Nonionic Surfactant | Alkylarylpolyalkoxylated glycols and derivatives |
| AD-SPRAY ® 90 | Nonionic Surfactant | Proprietary blend of alkylarylpolyalkoxylated glycols and derivatives |
| AERO DYNE-AMIC ® | Methylated or Ethylated Vegetable Oil, Nonionic Surfactant, Buffering Agent or Acidifier | Proprietary blend of ethoxylated alkyl phosphate esters, polyalkylene modified polydimethylsiloxane, nonionic emulsifiers and methylated vegetable oils |
| AGRI-DEX ® | Crop Oil (Petroleum) Concentrate | Proprietary blend of heavy range paraffin base petroleum oil, polyol fatty acid esters polyethoxylated derivatives |
| BLENDEX ® VHC | Compatibility Agent | Proprietary blend of alkylarylpolyethanol phosphate esters and other ethoxylated derivatives |
| CIDE WINDER ® | High Surfactant Oil Concentrate | Ethoxylated alkyl phosphate esters, nonionic surfactants, and $C_{16}$-$C_{18}$ alkanoates |
| COHORT ® DC | Nonionic Surfactant | Blend of alcohol ethoxylates and organic nitrogen |
| COTTON OIL PLUS ® | Vegetable Oil Concentrate, Deposition (Drift Control) and/or Retention Agent, Buffering Agent or Acidifier | Cottonseed oil plus nonionic blend of alkoxylated alkylated alkylphenols and fatty acids (85:15) |
| CROP OIL CONCENTRATE ® | Crop Oil (Petroleum) Concentrate | Paraffin based petroleum oil plus polyoxyethylated polyol fatty acid esters, and polyol fatty acid esters (83:17) |
| DROP ZONE ® LC | Deposition (Drift Control) and/or Retention Agent, Crop Oil (Petroleum) Concentrate | Guar gum dispersed in paraffin oil |
| DYNA-PAK ® | Surfactant plus Nitrogen Source | Alkanoates, nonionic surfactants, and carbamide salts |
| DYNE-AMIC ® | Methylated or Ethylated Vegetable Oil, Organo-Silicone Surfactant, Nonionic Surfactant | Proprietary blend of polyethoxylates dimethyl siloxanes, alkylaryl ethoxylates and methylated seed oils |
| INDUCE ® | Nonionic Surfactant | Alkylarylpolyoxyalkane ether and free fatty acids |
| INDUCE ® PH | Nonionic Surfactant | Proprietary blend of alkylarylpolyoxylkane ethers, alkylarylpolyethoxyethanol phosphates, free fatty acids plus buffering agents and other components |
| JOINT VENTURE ® | Nonionic Surfactant | Proprietary blend of polyalkyleneoxide, modified organosilicones, alkylpolyoxyalkane, ether, and aliphatic ester of $C_9$-$C_{12}$ fatty acids |
| KINETIC ® | Organo-Silicone Surfactant | Proprietary blend of polyalkyleneoxide modified polydimethylsiloxane and polyoxypropylene-polyoxyethylene block copolymers |
| KINETIC ® HV | Organo-Silicone Surfactant | Proprietary blend of polyalkyleneoxide modified polydimethylsiloxane and polyoxypropylene-polyoxyethylene block copolymers |
| MSO ® | Methylated or Ethylated Vegetable Oil | Proprietary blend of methylated oils and nonionic surfactant |

TABLE 1-continued

Adjuvants listed by brand name

| Brand Name | Adjuvant type | Main functional components |
| --- | --- | --- |
| OPTIMA ® | Buffering Agent or Acidifier | Proprietary blend of polyethoxylated alkyl amines, alkyl polyoxyethylene glycols and organic acids |
| PENETRATOR ® | Crop Oil (Petroleum) Concentrate, Deposition (Drift Control) and/or Retention Agent | Light range paraffin based petroleum oil and polyol fatty acid esters, and polyethoxylated derivatives |
| PENETRATOR ® PLUS | Crop Oil (Petroleum) Concentrate, Deposition (Drift Control) and/or Retention Agent, Buffering Agent or Acidifier | Mid-range mineral oil, polyol fatty acid esters, polyethoxylated ester thereof, ethoxylated alkyl phosphate esters |
| SILWET L-77 ® | Organo-Silicone Surfactant | Polyalkyleneoxide modified heptamethylsiloxane |
| SOY-DEX PLUS ® | Vegetable Oil Concentrate, Deposition (Drift Control) and/or Retention Agent, Buffering Agent or Acidifier | Proprietary blend of vegetable oil, polyol fatty acid ester, polyethoxylated esters thereof, ethoxylated alkylaryl phosphate ester |
| STRIKE ZONE ® DF | Deposition (Drift Control) and/or Retention Agent | Saccharide and polysaccharide ethers and alkyl polyethoxylated alcohols |
| TRANSACTIVE ® | Basic Blend, Surfactant plus Nitrogen Source, Buffering Agent or Acidifier | Blend of nonionic surfactant, ammonia salts and buffering agents |
| VEGETABLE OIL CONCENTRATE ® | Vegetable Oil Concentrate, Deposition (Drift Control) and/or Retention Agent | Vegetable oil plus nonionic blend of alkyloxylated alkylphenols and fatty acids (85:15) |

In a particular embodiment of the invention the adjuvant comprises or is at least one alkoxylated aliphatic alcohol of the formula (A), hereinafter also termed as alkoxylate A,

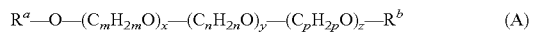  (A)

in which
$R^a$ represents $C_8$-$C_{36}$-alkyl, $C_8$-$C_{36}$-alkenyl or a mixture thereof, in particular $C_{10}$-$C_{32}$-alkyl, $C_{10}$-$C_{32}$-alkenyl, or a mixture thereof, more particularly $C_{14}$-$C_{26}$-alkyl, $C_{14}$-$C_{26}$-alkenyl, or a mixture thereof, especially $C_{15}$-$C_{20}$-alkyl, $C_{15}$-$C_{20}$-alkenyl, or a mixture thereof;
$R^b$ represents H or $C_1$-$C_{12}$-alkyl, in particular H or $C_1$-$C_4$-alkyl, more particularly H or methyl, especially H;
m, n, p represent, independently of one another, an integer from 2 to 16, in particular an integer from 2 to 5, more particularly an integer 2 or 3 (i.e. all of m, n, p are either 2 or 3, or one of m, n, p is 2 and the remaining two are both 3, or one of m, n, p is 3 and remaining two are both 2), specifically one of m, n, p is 2 and the remaining two are both 3 or one of m, n, p is 3 and the remaining two are both 2;
x, y, z represent, independently of one another, a number from 0 to 50, in particular a number from 0 to 30, especially a number from 0 to 20; and
x+y+z corresponds to a value from 2 to 50, in particular from 5 to 50, more particularly from 10 to 30 and especially from 12 to 20.

The term "alkoxylated" in this context means that the OH moiety of the aliphatic alcohol has been replaced by a polyoxyalkylene or polyalkylene oxide moiety. Polyoxyalkylene, in terms of the present invention, is an aliphatic polyether radical which is build from alkylene oxide repeating units A-O, where A is alkandiyl, in particular $C_2$-$C_5$-alkandiyl. Polyoxyalkylene, in terms of the present invention, is preferably a poly-$C_2$-$C_5$-alkylene oxide moiety, more preferably a poly-$C_2$-$C_4$-alkylene oxide moiety, especially a poly-$C_2$-$C_3$-alkylene oxide moiety, e.g. a polyethylene oxide moiety, a polypropylene oxide moiety, a poly(ethylene oxide-co-propylene oxide) moiety, a poly(ethylene oxide-co-butylene oxide) moiety or a poly(ethylene oxide-co-pentylene oxide) moiety. The number of alkylene oxide repeating units in the polyoxyalkylene radical is generally from 1 to 100 or from 2 to 100, preferably from 5 to 40, more preferably from 10 to 30 and in particular from 12 to 20.

The variable $R^a$ of the at least one alkoxylated alcohol of formula A may be linear or branched, preferably it is linear. $R^a$ may be saturated or unsaturated, preferably it is saturated. $R^a$ may be substituted or unsubstituted, preferably it is unsubstituted. Preferably, $R^a$ represents linear $C_8$-$C_{36}$-alkyl, $C_8$-$C_{36}$-alkenyl, or a mixture thereof. More preferably, $R^a$ represents linear $C_{14}$-$C_{36}$-alkyl, $C_{14}$-$C_{36}$-alkenyl, or a mixture thereof, in particular linear $C_{14}$-$C_{26}$-alkyl, $C_{14}$-$C_{26}$-alkenyl, or mixture thereof. Even more preferably, $R^a$ represents a linear $C_{14}$-$C_{22}$-alkyl, or a mixture thereof. Especially preferred, $R^a$ represents a linear $C_{16}$-$C_{20}$-alkyl, or a mixture thereof.

$R^b$ represents preferably H or methyl, in particular H.

Preferably, m, n, p represent, independently of one another, an integer from 2 to 5, more preferably an integer 2 or 3, specifically one of m, n, p is 2 and the remaining two are both 3 or one of m, n, p is 3 and the remaining two are both 2.

Preferably, x, y, z represent, independently of one another, a number from 0 to 30, more preferably from 0 to 20.

Preferably, the sum x+y+z corresponds to a value from 5 to 50, more preferably from 10 to 30, more preferably from 8 to 25, and in particular from 12 to 20.

According to a particular embodiment, alcohol alkoxylates of the formula (A) are used in which m=2 and the value of x is greater than zero. This relates to alcohol alkoxylates of the EO type to which belong especially alcohol ethoxylates (m=2; x>zero; y and z=zero) and alcohol alkoxylates with an EO block bonded to the alcohol portion that include further alkylene oxide moieties (m=2; x>zero; y and/or z>zero). As regards to the latter compounds, mention may also be made of EO-PO block alkoxylates (m=2; x>zero; y>zero; n=3; z=0), EO-PeO block alkoxylates (m=2; x>zero; y>zero; n=5; z=0) and EO-PO-EO block alkoxylates (m, p=2; x, z>zero; y>zero; n=3). In particular preferred are EO-PO block alkoxylates (m=2; x>zero; y>zero; n=3; z=0).

Here and in the following EO represents $CH_2CH_2O$, PO represents $CH(CH_3)CH_2O$ or $CH_2CH(CH_3)O$, BuO represents $CH(C_2H_5)CH_2O$, $C(CH_3)_2CH_2O$, $CH_2C(CH_3)_2O$, $CH(CH_3)CH(CH_3)O$ or $CH_2CH(C_2H_5)O$ and PeO represents ($C_5H_{10}O$).

In this context preference is given to EO-PO block alkoxylates in which the ratio of EO to PO (x to y) is 10:1 to 1:15, preferably 1:1 to 1:12 and in particular 1:2 to 1:8, with the degree of ethoxylation (value of x) being generally 1 to 20, preferably 2 to 15 and in particular 2 to 10 and the degree of propoxylation (value of y) being generally 1 to 30, preferably 4 to 20 and in particular 8 to 16. The overall degree of alkoxylation, i.e. the sum of EO and PO units, is generally 2 to 50, preferably 4 to 30 and in particular 6 to 20.

In this context preference is furthermore given to EO-PeO block alkoxylates in which the ratio of EO to PeO (x to y) is 2:1 to 25:1 and in particular 4:1 to 15:1, with the degree of ethoxylation (value of x) being generally 1 to 50, preferably 4 to 25 and in particular 6 to 15 and the degree of pentoxylation (value of y) being generally 0.5 to 20, preferably 0.5 to 4 and in particular 0.5 to 2. The overall degree of alkoxylation, i.e. the sum of EO and PeO units, is generally 1.5 to 70, preferably 4.5 to 29 and in particular 6.5 to 17.

According to a further particular embodiment, alcohol alkoxylates of the formula (A) are used in which n=2, the values of x and y are both greater than zero and z=0. This relates to alcohol alkoxylates of the EO type in which the EO block is terminally bonded. These include especially PO-EO block alkoxylates (n=2; x>zero; y>zero; m=3; z=0) and PeO-EO block alkoxylates (n=2; x>zero; y>zero; m=5; z=0).

In this context preference is given to PO-EO block alkoxylates in which the ratio of PO to EO (x to y) is 1:10 to 15:1, preferably 1:1 to 12:1 and in particular 2:1 to 8:1, with the degree of ethoxylation (value of y) being generally 1 to 20, preferably 2 to 15 and in particular 2 to 10, and the degree of propoxylation (value of x) being generally 0.5 to 30, preferably 4 to 20 and in particular 6 to 16. The overall degree of alkoxylation, i.e. the sum of EO and PO units, is generally 1.5 to 50, preferably 2.5 to 30 and in particular 8 to 20.

In this context preference is also given to PeO-EO block alkoxylates in which the ratio of PeO to EO (x to y) is 1:50 to 1:3 and in particular 1:25 to 1:5, with the degree of pentoxylation (value of x) being generally 0.5 to 20, preferably 0.5 to 4 and in particular 0.5 to 2 and the degree of ethoxylation (value of y) being generally 3 to 50, preferably 4 to 25 and in particular 5 to 15. The overall degree of alkoxylation, i.e. the sum of EO and PeO units, is generally 3.5 to 70, preferably 4.5 to 45 and in particular 5.5 to 17.

In an especially preferred embodiment the alkoxylate is selected from alkoxylated alcohols of the formula (A), in which $R^a$ represents linear $C_{12}$-$C_{22}$-alkyl, especially linear $C_{10}$-$C_{20}$ alkyl or a mixture thereof;

$R^b$ represents H or $C_1$-$C_4$-alkyl, preferably H or methyl, in particular H;

m, n, p represent, independently of one another, an integer from 2 to 5, preferably 2 or 3;

x, y, z represent, independently of one another, a number from 0 to 50; and x+y+z corresponds to a value from 5 to 50, preferably from 8 to 25.

In a further particular embodiment, the surface active substance comprises at least one anionic emulsifier as a component c.2). The amount of component c.2), if present, is generally from 0.1 to 30% by weight, preferably 0.5 to 20% by weight, in particular 1 to 10% by weight, and specifically 2 to 8% by weight, based on the total weight of the formulation.

Suitable anionic surfactants in this context are, in principle, all anionic surfactants typically used for stabilizing aqueous o/w emulsions. These are generally organic compounds having a hydrophobic radical, typically a hydrocarbon radical having 6 to 40, frequently 6 to 30 and in particular 8 to 22, carbon atoms and at least one functional group which, in aqueous media, is present in anionic form, for example a carboxylate, sulfonate, sulfate, phosphonate, phosphate, hydrogenphosphate or dihydrogenphosphate group. If appropriate, the anionic surfactants additionally have a poly-$C_2$-$C_3$-alkylene ether group, in particular a polyethylene oxide group having 1 to 50, in particular 2 to 30, $C_2$-$C_3$-alkylene oxide repeat units, in particular ethylene oxide repeat units.

Preferred anionic surfactants are those having at least one $SO_3$ group (sulfate and/or sulfonate) or one $PO_4$ group (phosphate group). From among these, preference is given to those anionic surfactants having at least one and in particular one aliphatic hydrocarbon radical having 8 to 22 carbon atoms or one araliphatic hydrocarbon radical having 10 to 26 carbon atoms. Such anionic surfactants are typically employed in the form of their alkali metal salts, alkaline earth metal salts or ammonium salts, in particular in the form of their sodium, potassium, calcium or ammonium salts. Here and below, the term "aliphatic" is meant to include alkyl, alkenyl and alkadienyl and preferably denotes alkyl. The term "aralkyl" denotes an aromatic hydrocarbon radical, such as phenyl or naphthyl, and preferably denotes phenyl having one or more, in particular one, alkyl group.

Examples of such anionic surfactants are:

c.2.1. $C_8$-$C_{22}$-alkylsulfonates, such as laurylsulfonate and isotridecylsulfonate;

c.2.2. $C_8$-$C_{22}$-alkyl sulfates, such as lauryl sulfate, isotridecyl sulfate, cetyl sulfate and stearyl sulfate;

c.2.3. aryl- and $C_1$-$C_{22}$-alkylarylsulfonates, e.g. naphthalenesulfonate, mono-, di- and tri-$C_1$-$C_{16}$-alkylnaphthylsulfonates such as dibutylnaphthylsulfonate, mono-, di- and tri-$C_1$-$C_{22}$-alkylbenzenesulfonates such as cumenesulfonate, nonylbenzenesulfonate, dodecylbenzenesulfonate and isotridecylbenzenesulfonate, or dodecyldiphenylether sulfonate;

c.2.4. sulfates and sulfonates of fatty acids having preferably 8 to 22 carbon atoms and of fatty acid esters, for example sulfates and sulfonates of mono-, di- and triglycerides and of $C_1$-$C_{18}$-alkyl $C_8$-$C_{22}$-alkanoates;

c.2.5. sulfates of ethoxylated $C_8$-$C_{22}$-alkanols, for example the sulfates of ethoxylated lauryl alcohol, of ethoxylated isotridecanol, of ethoxylated $C_{16}$-$C_{18}$-alkanol mixtures, of ethoxylated stearyl alcohol, etc.;

c.2.6. sulfates of ethoxylated hydroxyaromatics, in particular sulfates of ethoxylated phenols, for example sulfates of ethoxylated $C_4$-$C_{22}$-alkylphenols, for example the sulfates of ethoxylated octylphenol, of ethoxylated nonylphenol, of ethoxylated dodecylphenol and of ethoxylated tridecylphenol, and also the sulfates of ethoxylated polyarylphenols, such as in particular sulfates of ethoxylated mono-, di- or tristyrylphenols;

c.2.7. phosphates of $C_8$-$C_{22}$-alkanols, of $C_4$-$C_{22}$-alkylphenols and of polyarylphenols, such as in particular of mono-, di- or tristyrylphenols;

c.2.8. phosphates of ethoxylated $C_8$-$C_{22}$-alkanols, of ethoxylated $C_4$-$C_{22}$-alkylphenols and of ethoxylated polyarylphenols, such as in particular of ethoxylated mono-, di- or tristyrylphenols;

c.2.9. mono- and di-$C_4$-$C_{22}$-alkyl esters of sulfosuccinic acid, such as dihexyl sulfosuccinate, dioctyl sulfosuccinate, and bis-2-ethylhexyl sulfosuccinate; and also c.2.10. condensates of naphthalenesulfonic acid or phenolsulfonic acid with formaldehyde and, if appropriate, urea; including the salts thereof, such as their alkali metal salts, alkaline earth metal salts or ammonium salts, in particular in the form of their sodium, potassium, calcium or ammonium salts.

Preferred anionic surfactants are those of groups c.2.3., c.2.6. and c.2.8. More preferably the anionic surfactants are selected from $C_1$-$C_{22}$-alkylarylsulfonates, sulfates of ethoxylated $C_4$-$C_{22}$-alkylphenols, sulfates of ethoxylated polyarylphenols, phosphates of ethoxylated $C_4$-$C_{22}$-alkylphenols and phosphates of ethoxylated polyarylphenols, even more preferably from mono-, di- and tri-$C_1$-$C_{22}$-alkylbenzenesulfonates, sulfates of ethoxylated $C_8$-$C_{22}$-alkylphenols, phosphates of ethoxylated $C_8$-$C_{22}$-alkylphenols, sulfates of ethoxylated mono-, di- or tristyrylphenols and phosphates of ethoxylated mono-, di- or tristyrylphenols, and in particular from mono-$C_8$-$C_{22}$-alkylbenzenesulfonates, sulfates and phosphates of ethoxylated $C_8$-$C_{22}$-alkylphenols and sulfates of ethoxylated di- or tristyrylphenols. Specifically, the at least one anionic surfactant for the liquid concentrate formulations of the present invention is a mono-$C_8$-$C_{20}$-alkylbenzenesulfonate. An example of these preferred surfactants is dodecylbenzenesulfonate, which is available for example under the trade names Wettol® EM1 (from BASF), Witconate™ P-1220EH (from AkzoNobel), Ninate® 401-A (from Stepan), Nansa® EMV 62/H (from Huntsman), and Calsogen® EH (from Clariant).

In yet a further particular embodiment, the surface active substance comprises at least one nonionic emulsifier, which is different from the aforementioned non-ionic surface active adjuvants, as a component c.3). The amount of component c.3), if present, is generally from 0.1 to 30% by weight, preferably 0.5 to 20% by weight, in particular 1 to 10% by weight, and specifically 2 to 8% by weight, based on the total weight of the formulation.

Suitable non-ionic surfactants which can be used as component c.3) are preferably selected from the group consisting of $C_2$-$C_3$-polyalkoxylates of $C_{10}$-$C_{22}$-hydroxy fatty acid triglycerides, $C_2$-$C_3$-polyalkoxylates of $C_{10}$-$C_{22}$-fatty acid mono- or diglycerides, ethoxylated $C_4$-$C_{22}$-alkylphenols such as ethoxylated octylphenol, ethoxylated nonylphenol, ethoxylated dodecylphenol and ethoxylated tridecylphenol and ethoxylated polyarylphenols such as ethoxylated distyrylphenol, ethoxylated tristyrylphenol and the formaldehyde condensation products of ethoxylated distyrylphenol or ethoxylated tristyrylphenol. The non-ionic surfactants of component c.3) are in particular selected from the group consisting of $C_2$-$C_3$-polyalkoxylates of $C_{10}$-$C_{22}$-hydroxy fatty acid triglycerides and $C_2$-$C_3$-polyalkoxylates of $C_{10}$-$C_{22}$-fatty acid mono- or diglycerides, preferably from the group consisting of polyethoxylates of $C_{12}$-$C_{22}$-hydroxyfatty acid triglycerides and polyethoxylates of $C_{12}$-$C_{22}$-fatty acid mono- or diclycerides. In particular the at least one non-ionic surfactants S of the inventive formulations is selected from polyethoxylates of $C_{12}$-$C_{22}$-hydroxyfatty acid triglycerides, specifically from polyethoxylates of castor oil. Polyethoxylates of castor oils are available for example under the tradenames Emulpon™ CO-550 (from AkzoNobel), Wettol® EM31 (from BASF), Stepantex® CO-30 (from Stepan), Agnique® CSO-30 (from Cognis), Cirrasol™ G-1282 (from Croda) and Emulsogen® EL 360 (from Clariant). The average degree of ethoxylation in the surfactant of component c.3) is usually from 10 to 150, preferably from 15 to 100, in particular from 20 to 70 and specifically from 30 to 65.

In yet a further particular embodiment, the surface active substance comprises as a component c.4) at least one non-ionic block copolymer P comprising at least one polyethylene oxide moiety PEO and at least one polyether moiety PAO consisting of repeating units derived from $C_3$-$C_4$-alkylene oxides and/or styrene oxide, where the block copolymer P does not have alkyl or alkenyl groups with more than 6 carbon atoms. The amount of component c.4), if present, is generally from 0.1 to 20% by weight, preferably 0.2 to 15% by weight, in particular 0.5 to 10% by weight, and specifically 1 to 8% by weight, based on the total weight of the formulation.

The PAO moiety in the non-ionic block copolymer P usually comprises at least 3, preferably at least 5, in particular 10 to 100 repeating units (number average) which are derived from $C_3$-$C_6$ alkylene oxides, such as propylene oxide, 1,2-butylene oxide, cis- or trans-2,3-butylene oxide or isobutylene oxide, 1,2-pentene oxide, 1,2-hexene oxide or styrene oxide. Thus, the PAO moieties can be described by the general formula $(\text{—O—CHR}^x\text{—CHR}^y\text{—})_q$, wherein q is the number of repeating units in the PAO moiety, $R^x$ and $R^y$ are independently selected from $C_1$-$C_4$ alkyl and hydrogen, provided that at least one of the radicals $R^x$, $R^y$ is different from hydrogen and the total number of carbon atoms of $R^x$ and $R^y$ in one repeating unit is from 1 to 4. One of the radicals $R^x$ or $R^y$ may also be a phenyl radical while the other is hydrogen.

Preferably, the repeating units in the PAO moiety are derived from $C_3$-$C_4$-alkylene oxides, in particular from propylene oxide. Preferably, the PAO moieties comprise at least 50% by weight and more preferably at least 80% by weight of repeating units derived from propylene oxide. If the PAO moiety comprises different repeating units, these different repeating units may be arranged statistically or preferably block wise.

According to a preferred embodiment of the invention the at least one polyether moiety PAO of the block copolymer P consists of repeating units derived from propylene oxide.

The PEO moieties of the non-ionic block copolymer P usually comprise at least 3, preferably at least 5, and more preferably at least 10 repeating units derived from ethylene oxide (number average). Thus, the PEO moiety can be described by the general formula $(\text{CH}_2\text{—CH}_2\text{—O})_p$, wherein p is the number of repeating units within the PEO moiety.

The total number of ethylene oxide repeating units in the PEO moiety or moieties and repeating units in the PAO moiety will usually be in the range from 3 to 1,000, preferably 4 to 500 and in particular 5 to 150 (number average). Among the non-ionic block copolymers P those are preferred which have a number average molecular weight $M_N$ ranging from 400 to 50,000 Dalton, preferably from 500 to 10,000 Dalton, more preferably from 750 to 6,000 Dalton and in particular from 1000 to 5,000 Dalton.

The weight ratio of PEO moieties to PAO moieties (PEO:PAO) in the non-ionic block copolymer P usually ranges from 1:10 to 10:1, preferably from 1:10 to 3:1, more preferably from 2:8 to 7:3 and in particular from 3:7 to 6:4.

In general, the PEO moieties and the PAO moieties in the non-ionic block copolymer P make up at least 80% by weight and preferably at least 90% by weight, e.g. 90 to 99.5% by weight of the non-ionic block copolymer P.

Among the block copolymers P those are preferred which have a HLB-value ranging from 5 to 20 and in particular from 7 to 18. The HLB value (hydrophilic lipophilic balance) referred to herein is the HLB value according to Griffin (W. C. Griffin, J. Soc. Cosmet. Chem. 1, 311 (1950); 5, 249 (1954)—see also P. Becher et al, Non-ionic surfactants, Physical Chemistry, Marcel Dekker, N.Y. (1987), pp. 439-456; H. Mollet et al. "Formulation Technology", $1^{st}$ ed. Wiley-VCH Verlags GmbH, Weinheim 2001, pages 70-73 and references cited therein).

Preferred block copolymers for use in the formulations of the invention can be described by the following formulae P1 to P5:

$R^1$—PEO—O—PAO—$R^2$      P1

$R^1$—PAO—O—PEO—H      P2

$R^3$—PEO—PAO—NR—PAO'—PEO'—$R^4$      P3

$R^3$—PEO—PAO—(O-A)$_n$-O—PAO'—PEO'—$R^4$      P4

$R^3$—PEO—PAO—$NR^a$-A'-$NR^b$—PAO'—PEO'—$R^4$      P5 wherein n is 0 or 1,

A, A' are each a bivalent organic radical which has 2 to 20 carbon atoms and which may carry 1 or 2 hydroxy groups and/or 1, 2, 3 or 4 ether moieties and which may also carry 1 or 2 radicals of the formula $R^2$—PEO—PAO—;

PAO, PAO' are identical or different and each, independently of one another, are a PAO moiety as defined above, in particular a poly-$C_3$-$C_4$-alkylene oxide moiety;

PEO, PEO' are polyethylene oxide moieties;

R is $C_1$-$C_6$-alkyl or a radical $R^2$—PEO—PAO—;

$R^1$ is $C_1$-$C_6$-alkyl or $C_1$-$C_6$-alkylphenyl;

$R^2$, $R^3$, $R^4$ are each, independently of one another, hydrogen, $C_1$-$C_6$-alkyl, $C_1$-$C_6$-alkylcarbonyl, or benzyl; and $R^a$, $R^b$ are each, independently of one another, hydrogen, $C_1$-$C_6$-alkyl or a radical $R^2$—PEO—PAO—.

A skilled person will readily understand that the radicals $R^1$, $R^2$, $R^3$ and $R^4$ in formulae P1 to P5 are linked to the PEO or PAO moiety via an oxygen atom.

$R^1$ and $R^2$ in formulae P1 and P2 are preferably $C_1$-$C_6$-alkyl, such as methyl, ethyl, n-propyl, isopropyl, n-butyl, 2-butyl, n-pentyl, n-hexyl and the like. $R^2$ in formula P1 is preferably hydrogen. $R^3$ and $R^4$ in formulae P3, P4 and P5 are preferably hydrogen. R in formula P3 is preferably $C_1$-$C_6$-alkyl, in particular $C_2$-$C_6$-alkyl.

Suitable radicals A and A' in formulae P4 and P5 may be aliphatic or cycloaliphatic radicals or aromatic radicals or mixed aromatic/aliphatic or mixed aliphatic/cycloaliphatic radicals. Examples for aliphatic radicals A and A' are $C_2$-$C_6$-alkandiyl and $C_2$-$C_{20}$-alkandiyl with 1, 2, 3 or 4 $CH_2$-moieties being replaced by oxygen or sulfur, e.g. ethane-1,2-diyl, propane-1,3-diyl, butane-1,4-diyl, hexane-1,4-diyl, 3-oxapentane-1,5-diyl, 3-oxahexane-1,6-diyl, 4-oxaheptane-1,7-diyl, 3,6-dioxaoctane-1,8-diyl, 3,7-dioxanonane-1,9-diyl and 3,6,9-trioxaundecan-1,11-diyl. Examples of cycloaliphatic radicals A, A' comprise $C_5$-$C_6$-cycloalkanediyl, which may carry 1, 2, 3 or 4 $C_1$-$C_4$-alkyl groups, e.g. methyl groups, such as cyclohexane-1,2-, -1,3-, and -1,4-diyl. Aromatic radicals A, A' are for example 1,2-phenylene, 1,3-phenylene, 1,4-phenylene. Mixed aliphatic/aromatic radicals A, A' are those which comprise one or more alkanediyl units and at least one aromatic unit such as a phenyl ring. Examples for mixed aliphatic/aromatic radicals A, A' comprise diphenylmethane-4,4'-diyl, 4,4'-[2,2-bis (phenyl)propane]diyl and the like. Preferred radicals A, A' are selected from $C_2$-$C_6$-alkandiyl and $C_2$-$C_{20}$-alkandiyl with 1, 2, 3 or 4 $CH_2$-moieties being replaced by oxygen.

Amongst the non-ionic block copolymers P of formulae P1 to P5 those of formulae P2 and P4 are especially preferred. Particularly preferred are block copolymers P of formulae P2 and P4 wherein the PAO moieties are derived from propylene oxide.

In one embodiment of the invention the non-ionic block copolymer P comprises a terminal $C_1$-$C_6$-alkyl group, such as methyl, ethyl, n-propyl, isopropyl, n-butyl, isobutyl, sec-butyl, n-heptyl or n-hexyl, and in particular n-butyl. According to this embodiment preferred non-ionic block copolymers P are those of formula P1 with at least one of $R^3$ and $R^4$ being a $C_1$-$C_6$-alkyl group, those of formula P2 with $R^1$ being a $C_1$-$C_6$-alkyl group and those of formulae P3, P4 and P5, respectively, with at least one of $R^3$ and $R^4$ being a $C_1$-$C_6$-alkyl group. Particularly preferred non-ionic block copolymers P according to this embodiment are those of formula P2 with $R^1$ being a $C_1$-$C_6$-alkyl group, in particular butyl, and also those of formula P4 with at least one of $R^3$ and $R^4$ being a $C_1$-$C_6$-alkyl group, in particular butyl, and preferably n being 0.

According to the invention, a single type of non-ionic block copolymer P or different types of block copolymers P may be used. In a preferred embodiment of the invention the liquid pesticide formulation comprises a single type of non-ionic block copolymer P. In another preferred embodiment the liquid pesticide formulation comprises 2 different types of non-ionic block copolymers P. Different types means that the block copolymers are distinct with regard to at least one of the following features: molecular weight, weight ratio of PEO to PAO, the HLB-value or the molecular architecture. In case 2 different non-ionic block copolymers P are used, preferably one and more preferably both of the block copolymers combine at least two or all of the preferred features. In such mixtures the block copolymer P that combines at least two or all of the preferred features makes up at least 20% by weight, preferably at least 30% by weight, e.g. 20 to 90% by weight, in particular 30 to 80% by weight of the total amount of block copolymer P in the formulation.

Non-ionic block copolymers P are known in the art and commercially available under the trade names Pluronic®, such as Pluronic® P 65, P84, P 103, P 105, P 123 and Pluronic® L 31, L 43, L 62, L 62 LF, L 64, L 81, L 92 and L 121, Pluraflo® such as Pluraflo® L 860, L1030 and L 1060; Pluriol® such as Pluriol® WSB-125, Tetronic®, such as Tetronic® 704, 709, 1104, 1304, 702, 1102, 1302, 701, 901, 1101, 1301 (BASF SE), Agrilan® AEC 167 and Agrilan® AEC 178 (Akcros Chemicals), Antarox® B/848 (Rhodia), Berol® 370 and Berol® 374 (Akzo Nobel Surface Chemistry), Dowfax® 50 C15, 63 N10, 63 N30, 64 N40 and 81 N10 (Dow Europe), Genapol® PF (Clariant), Monolan®, such as Monolan® PB, Monolan® PC, Monolan® PK (Akcros Chemicals), Panox® PE (Pan Asian Chemical Corporation), Symperonic®, such as Symperonic® PE/L, Symperonic® PE/F, Symperonic® PE/P, Symperonic® PE/T (ICI Surfactants), Tergitol® XD, Tergitol® XH and Tergitol® XJ (Union Carbide), Triton® CF-32 (Union Carbide), Teric PE Series (Huntsman) and Witconol®, such as Witconol® APEB, Witconol® NS 500 K and the like. Likewise particular preference is given to poly(ethoxylate-co-propoxylates) of $C_1$-$C_6$ alkanols, having a number average molecular weight $M_N$ of from 1000 to 5000 Dalton Particularly preferred examples include Atlas® G 5000 (Croda), Tergitol®XD, Pluronic® P105 and Pluriol® WSB-125 and the like.

In yet a further particular embodiment, the surface active substance comprises the component c.1) and the component c.2).

In yet a further particular embodiment, the surface active substance comprises the component c.1) and the component c.3).

In yet a further particular embodiment, the surface active substance comprises the component c.1) and the component c.4).

In yet a further particular embodiment, the surface active substance comprises the component c.2) and the component c.3).

In yet a further particular embodiment, the surface active substance comprises at least one component c.3) selected from nonionic emulsifiers, different from the aforementioned non-ionic surface active adjuvants.

In a special embodiment, the surface active substance comprises the components c.1), c.2) and c.3).

In another special embodiment, the surface active substance comprises the components c.2), c.3) and c.4).

In yet a further special embodiment, the surface active substance comprises the components c.1), c.3) and c.4).

In a very special embodiment, the surface active substance comprises the components c.1), c.2), c.3) and c.4).

In a very special embodiment of the invention, the formulation comprises:
a) 1 to 10% by weight, especially 2 to 8% by weight, based on the total weight of the formulation, of the compound of formula I;
b) 30 to 70% by weight, based on the total weight of the formulation, of the organic solvent or solvent mixture;
c.1) 10 to 40% by weight, specifically 15 to 30% by weight, based on the total weight of the formulation, of at least one non-ionic surface active adjuvant as defined in claims 7 to 9;
c.2) 1 to 10% by weight, specifically 2 to 8% by weight, based on the total weight of the formulation, of at least one anionic emulsifier;
c.3) 1 to 10% by weight, specifically 2 to 8% by weight, based on the total weight of the formulation, of at least one non-ionic emulsifier different from the non-ionic surface active adjuvants;
c.4) optionally 0.5 to 10% by weight, specifically 1 to 8% by weight, based on the total weight of the formulation, at least one non-ionic block copolymer P as defined above;
where the total amount of components a), b), c.1), c.2), c.3) and, if present, component c.4) add up to at least 90% by weight, in particular at least 95% by weight, especially at least 99% by weight of the total amount of the formulation.

It is preferred to include at least one pH adjuster into the liquid concentrate formulation. The pH adjuster may be incorporated at any stage of the inventive process and is generally added prior to step ii), but it may also be added to the final formulation. The pH adjuster is a base, which is preferably selected from organic amines comprising at least one primary, secondary, and/or tertiary amino group. Preferred amines comprise at least one secondary and/or tertiary amino group, and in particular comprise at least one tertiary amino group.

The organic amines have typically a pH value of at least 7.0 (preferably at least 7.5, in particular at least 8.0) in water at 20° C. at a concentration of 0.1 mol/l. In other words, pH adjusters are preferably selected from those amines which form aqueous solutions having pH values of at least 7.0, preferably at least 7.5, in particular at least 8.0 at 20° C. at a concentration of 0.1 mol/l in water. Often, said pH value is in a range from 7.0 to 14.0, preferably from 7.5 to 12.0, and in particular from 8.0 to 10.0. Preferred amines are those, where the acidity constant $pK_a$ of the conjugate ammonium ion at 20° C. in water is generally at least 7.0, preferably at least 8.0, in particular at least 8.5, e.g. from 7.0 to 14, in particular from 8.0 to 13.0 and especially from 8.5 to 12.0.

Usually, the boiling point at 1013 mbar of the amine is at least 40° C., preferably at least 80° C., and in particular at least 150° C. Preferably, the amine is free of an aromatic group.

The amine has usually a solubility in water of at least 0.1 g/l at 20° C., preferably at least 1.0 g/l and in particular at least 10 g/l.

Examples of amines are ammonia ($NH_3$), 2-(2-aminoethoxy)ethanol (DGA), dimethylamine (DMA), N-aminopropylmorpholine (APM), tetraethylenepentamine (TEPA), dipropylene triamine, diethylenetriamine (DETA), tetra(2-hydroxypropyl)ethylenediamine (Quadrol®), triethanolamine (TEA), hexamethylenediamine, Jeffamine D-230, triisopropanolamine (TIPA), hexamethylenetetramine, diethylethanolamine (DEEA), DMF-DMA, 2-(diethylamino)ethylamine, 2-phenylethylamine, 3-(2-ethylhexoxy)propylamine, 3-ethoxypropylamine, 3-methoxypropylamine, butylamine, cyclohexylamine, di-2-ethylhexylamine (DEHA), dibutylamine, diethylamine (DEA), dipropylamine, dipropylene triamine, ditridecylamine (DTD amine), hexylamine, isopropylamine, pentamethyldiethylenetriamine (PM-DETA), methoxyisopropylamine, N,N-bis-3-aminopropylmethylamine (BAPMA), N,N-dimethylisopropylamine, N-ethyldiisopropylamine, N-octylamine, 3-(2-aminoethylamino)propylamine (N3-amine), propylamine, tributylamine, tridecylamine, tripropylamine, tris-(2-ethylhexyl)amine (TEHA), tert-butylamine (t-BA), diisopropanolamine (DIPA), N,N-dimethylethanolamine, N,N-dimethylisopropanolamine, N-methylethanolamine (NMEA), N-methyldiethanolamine (MDEA), 2,6-xylidine, dicykan, benzylamine, dimethylcyclohexylamine (DMCHA), N,N-dimethylbenzylamine (DMBA), N-(2-hydroxyethyl)aniline, o-toluidine, ethyl-(2-hydroxyethyl)aniline, 1,2-propylenediamine (1.2-PDA), 1,3-diaminopropane (DAP), dimethyldicykan (DMDC), 3-aminopropyldiethyleneglycol (mono-TTD), 4,7,10-trioxatridecane-1,13-diame (TTD), 4,9-dioxadodecane,1,12-diamine (DODA), dimethylaminopropylamine (DMAPA), ethylenediamine (EDA), isophoronediamine, triethylenediame (TEDA), bis (2-dimethylaminoethyl)ether (BDMAEE), N-(2-aminoethyl)ethanolamine (AEE), N-ethylpiperazine, 2,2-dimethyl-propane-1,3-diamine, piperazine, diethanolamine (DEA), N-ethylethanolamine (EEA), monoethanolamine (MEOA), N-(2-aminoethyl)ethanolamine, polyetheramine D 2000 (PEA D 2000), polyetheramine D 400 (PEA D 2000), polyetheramine T403, 1-methyl imidazole, 1-vinylimidazole, 2-ethyl imidazole, 2-methyl imidazole, imidazole, 1,2-dimethyl imidazole, morpholine, pyrrolidine, diisopropanol-p-toluidine (PIIPT), isopropanolamine, 2,2'-dimorpholinyldiethylether (DMDEE), N-ethylmorpholine (NEM), N-methylmorpholine, dimethylaminoethoxyethanol (DMEE), N,N'-dimethylpiperazine, trimethylaminoethylethanolamine (TMAEEA), S-triazine, 1,8-diazabicyclo-5,4,0-undecene-7, N-(3-aminopropyl)imidazole, N-butylethanolamine (BEA), 34(2-hydroxyethyl)amino)propanol, 3-amino-1-propanol, 3-dimethylaminopropane-1-ol, aminoethylethanolamine (AEEA), N-methylmorpholine oxide (NMMO), N-aminoethylpiperazine (AEP), dimethylpiperazine (DMP), methoxypropylamine (MOPA), tetramethylbis (aminoethyl)ether (ZF-20), N,N-dimethyl-2(2-aminoethoxy)ethanol (ZR-70), pentamethyldipropylenetriamine (ZR-40), tetramethyldipropylenetriamine (Z-130), benzyldimethylamine (BDMA), triethylenetetramine (TETA), Jeffamine® D-400, monoisopropanolamine (MIPA).

Further suitable amines are amines which comprise an alkoxylated amino group. Preferred are alkoxylated $C_{8-24}$ fatty amines, especially ethoxylated $C_{12-20}$ fatty amines. Examples are ethoxylated coco amine, POE 2 (Agnique® CAM-2), ethoxylated coco amine, POE 10 (Agnique® CAM-10), ethoxylated coco amine, POE 15 (Agnique® CAM-15), ethoxylated coco amine, POE 20 (Agnique® CAM-20), ethoxylated oleyl amine, POE 30 (Agnique® OAM-30), ethoxylated tallow amine, POE 5 (Agnique® TAM-5), ethoxylated tallow amine, POE 10 (Agnique® TAM-10), ethoxylated tallow amine, POE 15 (Agnique® TAM-15), ethoxylated tallow amine, POE 20 (Agnique® TAM-20), ethoxylated tallow amine, POE 50 (Agnique® TAM-50), ethoxylated stearyl amine, POE 50 (Agnique® SAM-50). The Agnique product series is available from Cognis.

Suitable organic amines are in particular those of the formula III

(III)

where:
$R^1$ is H, $C_1$-$C_4$-alkyl, or a radical $(A-O)_nH$, in particular a radical of the formula $(A-O)_nH$,
A is $C_2$-$C_4$-alkandiyl, in particular 1,2-ethandiyl or 1,2-propandiyl,
m is an integer from 1 to 100, in particular 1 to 50, m may also be 0, if at least one of $R^1$, $R^2$ and in particular both $R^1$ and $R^2$ is/are different from H;
n is an integer from 1 to 100, in particular 1 to 50,
$R^2$ is H, $C_1$-$C_{30}$ alkyl, $C_2$-$C_{30}$ alkenyl or a radical of formula $-[A'-N(R^3)]_k-A'-NR^4R^5$, where
A' is $C_2$-$C_4$-alkandiyl, in particular 1,2-ethandiyl, 1,2-propandiyl, 1,3-propandiyl or 1,4-butandiyl,
k is an integer from 0 to 10, in particular 0, 1 or 2,
$R^3$ is H, $C_1$-$C_4$-alkyl, or a radical $(A-O)_nH$, in particular a radical $(A-O)_nH$,
$R^4$ is H, $C_1$-$C_4$-alkyl, or a radical $(A-O)_nH$, in particular a radical $(A-O)_nH$, and
$R^5$ is H, $C_1$-$C_4$-alkyl, or a radical $(A-O)_nH$, in particular a radical $(A-O)_nH$, or $NR^4R^5$ represent an N-bound pyrrolidinyl, piperidinyl, piperazinyl or morpholinyl radical.

Here and in the following, the suffix $C_n$-$C_m$ indicates the number range for the number of possible carbon atoms of the respective radical. Hence, $C_1$-$C_{30}$ alkyl is a linear or branched alkyl radical having from 1 to 30 carbon atoms. Likewise, $C_2$-$C_{30}$ alkenyl is a linear or branched aliphatic radical having from 1 to 30 carbon atoms, which has at least 1, e.g. 1, 2 or 3 C=C-double bonds. $C_1$-$C_4$ Alkyl is a linear or branched alkyl radical having from 1 to 4 carbon atoms, examples including methyl, ethyl, n-propyl, isopropyl, n-butyl, 2-butyl, isobutyl (=2-methylpropan-1-yl) or tert.-butyl (=2-methylpropan-2-yl). $C_2$-$C_4$ Alkandiyl is a linear or branched divalent alkyl radical having from 2 to 4 carbon atoms, examples including 1,2-ethandiyl, 1,2-propandiyl, 1,3-propandiyl, 1,2-butandiyl, 1,3-butandiyl, 1,1-dimethylethan-1,2-diyl 1,2-dimethylethan-1,2-diyl or 1,4-butandiyl.

Amongst the amines of formula III those are preferred, where m is from 1 to 100, in particular from 1 to 50 and $R^1$ is a radical of the formula $(A-O)_nH$, where n is from 1 to 50 in particular from 1 to 20.

Amongst the amines of formula III those are preferred, where $R^2$ is $C_5$-$C_{30}$ alkyl, $C_5$-$C_{30}$ alkenyl or a radical of formula $-[A'-N(R^3)]_k-A'-NR^4R^5$, where A' is $C_2$-$C_4$-alkandiyl, in particular 1,2-ethandiyl, 1,2-propandiyl, 1,3-propandiyl or 1,4-butandiyl, k is an integer from 0 to 10, in particular 0, 1 or 2, $R^3$, $R^4$ and $R^5$, independently from each other are selected from the group consisting of H, $C_1$-$C_4$-alkyl and a radical $(A-O)_nH$, in particular a radical $(A-O)_nH$, where A and n are as defined above and were n is in particular from 1 to 50 and where A is in particular 1,2-ethandiyl or 1,2-propandiyl.

Amongst the amines of formula III those are particularly preferred, where $R^2$ is $C_5$-$C_{30}$ alkyl or $C_5$-$C_{30}$ alkenyl, especially $C_8$-$C_{24}$ alkyl or $C_8$-$C_{24}$ alkenyl, m is from 1 to 50, in particular from 2 to 50 and $R^2$ is a radical of the formula $(A-O)$—H, where A and n are as defined above and where n is in particular from 1 to 50, especially from 2 to 50 and where A is in particular 1,2-ethandiyl or 1,2-propandiyl.

Amongst the amines of formula III those are likewise preferred, where $R^2$ is radical of formula $-[N-N(R^3)]_k-A'-NR^4R^5$, where N is $C_2$-$C_4$-alkandiyl, in particular 1,2-ethandiyl, 1,2-propandiyl, 1,3-propandiyl or 1,4-butandiyl, k is as defined above, in particular 0, 1 or 2, $R^3$, $R^4$ and $R^5$, independently from each other are selected from the group consisting of H, $C_1$-$C_4$-alkyl and a radical $(A-O)_nH$, in particular a radical $(A-O)_nH$, where A and n are as defined above and where n is in particular from 1 to 10 and where A is in particular 1,2-ethandiyl or 1,2-propandiyl, m is from 1 to 50, in particular from 1 to 10 and $R^2$ is a radical of the formula $(A-O)_nH$, where A and n are as defined above and where n is in particular from 1 to 10 and where A is in particular 1,2-ethandiyl or 1,2-propandiyl.

Particularly preferred pH adjusters are amines which contain at least one secondary and/or tertiary amino group, especially those amines which contain at least one tertiary amino group, and amines which comprise an alkoxylated amino group, in particular those of the formula III, preferably alkoxylated $C_{8-24}$ fatty amines, in particular those of the formula III, where $R^2$ is $C_8$-$C_{24}$ alkyl or $C_8$-$C_{24}$ alkenyl, in particular $C_{10}$-$C_{22}$ alkyl or $C_{10}$-$C_{22}$ alkenyl, m is from 1 to 50, in particular from 2 to 50 and $R^2$ is a radical of the formula $(A-O)_nH$, where A and n are as defined above and where n is in particular from 1 to 50, especially from 2 to 50 and where A is in particular 1,2-ethandiyl or 1,2-propandiyl. Examples such fatty amines include ethoxylated coco amine, POE 2 (Agnique® CAM-2), ethoxylated coco amine, POE 10 (Agnique® CAM-10), ethoxylated coco amine, POE 15 (Agnique® CAM-15), ethoxylated coco amine, POE 20 (Agnique® CAM-20), ethoxylated oleyl amine, POE 30 (Agnique® OAM-30), ethoxylated tallow amine, POE 5 (Agnique® TAM-5), ethoxylated tallow amine, POE 10 (Agnique® TAM-10), ethoxylated tallow amine, POE 15 (Agniqu® TAM-15), ethoxylated tallow amine, POE 20 (Agnique® TAM-20), ethoxylated tallow amine, POE 50 (Agnique® TAM-50), ethoxylated stearyl amine, POE 50 (Agnique® SAM-50).

The pH adjuster, if present, is generally included into the formulation in an amount of 0.001 to 10% by weight, preferably 0.01 to 7% by weight, in particular 0.03 to 4% by weight, and specifically 0.05 to 2% by weight, based on the total weight of the formulation.

It may also be possible to include further auxiliaries into the formulation. Examples for suitable further auxiliaries are organic and inorganic thickeners, bactericides, anti-foaming agents, and, if appropriate, colorants and tackifiers or binders (e. g. for seed treatment formulations).

The formulations prepared by the process of the invention may comprise small amounts of water, which generally does not exceed 5% by weight, based on the total weight of the formulation. In particular, the formulation does not comprise water or virtually does not comprise water, i.e. the amount of water is less than 5% by weight and in particular less than 2% by weight, based on the total weight of the formulation.

The formulations obtained by the process of the present invention can be used for controlling insects, arachnids or nematodes. Such a use generally comprises contacting an insect, acarid or nematode or their food supply, habitat, breeding grounds or their locus with the formulation or a dilution thereof in pesticidally effective amounts.

The formulations obtained by the process of the present invention can be applied in a conventional manner, e.g. in diluted form as an aqueous ready-to-use preparation. Such an aqueous ready-to-use preparations can be applied by spraying, in particular spraying of the leaves. Application can be carried out using spraying techniques known to the person skilled in the art, for example using water as carrier and amounts of spray liquor of about 100 to 1000 liters per hectare, for example from 300 to 400 liters per hectare.

The aqueous ready-to-use preparations are generally prepared by diluting the formulation with water, generally with at least 5 parts of water, preferably at least 10 parts of water, in particular at least 20 parts of water and more preferably at least 50 parts of water, e.g. from 10 to 10,000, in particular from 20 to 1,000 and more preferably from 50 to 250 parts of water per one part of the liquid formulation (all parts are given in parts by weight). Dilution will be usually achieved by pouring the liquid concentrate formulation into water. Usually, dilution is achieved with agitation, e.g. with stirring, to ensure a rapid mixing of the concentrate in water. However, agitation is generally not necessary. Though the temperature of mixing is not critical, mixing is usually performed at temperatures ranging from 0 to 100° C., in particular from 10 to 50° C. or at ambient temperature. The water used for mixing is usually tap water. However the water may already contain water soluble compounds which are used in plant protection, e.g. nutrificants, fertilizers or water soluble pesticides.

With regard to further details regarding the use of the aqueous suspension concentrate formulations obtained by the process of the invention reference is made to EP 2223599 and WO 2012/035015.

The following examples further illustrate the present invention:

EXAMPLES

Starting Materials

Insecticide A: Compound of formula I in the form of a crystalline solvate with ethyl benzene having an a.i. content of about 95% by weight.
Solvent: aromatic hydrocarbon solvent—Aromatic® 200 ND (ExxonMobil).
Adjuvant A: alkoxylated fatty alcohol of formula A—Plurafac® LF 1300 (BASF), liquid at room temperature, wetting power by immersion: >300 s (according to DIN 1772 at 1 g/L in 2 g/l sodium carbonate at 23° C.), water content 5-10% by weight, surface tension: ca. 32 mN/m (according to DIN 14370 at 1 g/L at 23° C.);
Adjuvant B: Agri-Dex® from Helena Chemical Company: Proprietary blend of heavy range paraffin base petroleum oil, polyol fatty acid esters and polyethoxylated derivatives;
Adjuvant C: MSO: Proprietary blend of methylated seed oils and nonionic polyethoxylated surfactant;
Adjuvant D: Silwet® L-77 from Helena Chemical Company, containing 84% of polyalkyleneoxide modified heptamethyltrisiloxanea and 16% of allyloxypolyethyleneglycol methyl ether,
Adjuvant E: Dyn-Amic® from Helena Chemical Company: Proprietary blend of polyethoxylated dimethyl siloxanes, alkylaryl ethoxylates and methylated seed oils;
Anionic Surfactant c.2: dodecylbenzenesulfonate (an anionic surfactant)—Witconate™ P-1220EH (AkzoNobel).
Non-ionic Surfactant c.3: ethoxylated castor oil (a non-ionic surfactant S)—Emulpon™ CO-550 (from AkzoNobel).
Block Copolymer c.4: n-butoxylated propylene oxide/ethylene oxide block copolymer (Non-ionic block copolymer P) with an HLB value of 17—Atlas G 5000 (Croda).
pH Adjuster A: N,N,N',N'-tetrakis-(2-hydroxypropyl)ethylene-diamine—Quadrol® (BASF SE).

Comparative Example 1

A solution of Insecticide A (pyripyropene derivative I) in the aromatic hydrocarbon solvent was prepared by slowly adding 4.98 parts by weight of insecticide A to well agitated 63.92 parts by weight of the solvent at room temperature. It typically took 1 to 3 hours for complete dissolution depending on the addition rate of insecticide A and on the mode of agitation. Then 19.9 parts by weight of adjuvant A, 6 parts by weight of surfactant c.2, 4 parts by weight of surfactant c.3, 1 part by weight of blockcopolymer c.4) and 0.2 parts by weight of the pH adjuster were added and the mixture was stirred until a homogenous and uniform solution was obtained. The thus prepared formulation was kept at 22° C. for two days. During that time a significant portion of the insecticide A crystallized from the solution.

Example 1

A solution of Insecticide A (pyripyropene derivative I) in the aromatic hydrocarbon solvent was prepared by slowly adding 4.98 parts by weight of insecticide A to well agitated 63.92 parts by weight of the solvent at room temperature. It typically took 1 to 3 hours for complete dissolution depending on the addition rate of insecticide A and on the mode of agitation. Then 19.9 parts by weight of adjuvant A, 6 parts by weight of surfactant c.2, 4 parts by weight of surfactant c.3, 1 part by weight of blockcopolymer c.4) and 0.2 parts by weight of the pH adjuster were added and the mixture was stirred until a homogenous and uniform solution was obtained. The thus prepared formulation was heated to 65° C. for 12 h.

Samples of the thus obtained formulation were then kept under various storage conditions for 1 month (22° C., −20° C. and cycling temperatures between −10° C. and +10° C. every 48 h). All samples remained clear and no crystalline material was formed. All samples could be easily diluted with water.

Comparative Example 2

A formulation was prepared by the method described for comparative example 1, replacing adjuvant A by the same amount of adjuvant B. Samples of the thus obtained formulation were then kept under various storage conditions for 3 weeks (22° C. and cycling temperatures between −10° C. and +10° C. every 48 h). In all samples a crystalline sediment was formed.

Example 2

A solution of Insecticide A (pyripyropene derivative I) in aromatic hydrocarbon solvent was prepared by slowly adding 4.98 parts by weight of insecticide A to well agitated 63.92 parts by weight of the solvent at room temperature. It typically took 1 to 3 hours for complete dissolution depending on the addition rate of insecticide A and on the mode of agitation. Then 19.9 parts by weight of adjuvant B, 6 parts by weight of surfactant c.2, 4 parts by weight of surfactant c.3, 1 part by weight of blockcopolymer c.4) and 0.2 parts by weight of the pH adjuster were added and the mixture was stirred until a homogenous and uniform solution was obtained. The thus prepared formulation was heated to 65° C. for 4 h.

Samples of the thus obtained formulation were then kept under various storage conditions for 3 weeks (22° C., −20° C. and cycling temperatures between −10° C. and +10° C. every 48 h). All samples remained clear and no crystalline material was formed. All samples could be easily diluted with water.

Example 3

A formulation was prepared by the method described for example 2, replacing adjuvant B by the same amount of adjuvant C. Samples of the thus obtained formulation were then kept under various storage conditions for 3 weeks (22° C., −20° C. and cycling temperatures between −10° C. and +10° C. every 48 h). All samples remained clear and no crystalline material was formed. All samples could be easily diluted with water.

Example 4

A formulation was prepared by the method described for example 2, replacing adjuvant B by the same amount of adjuvant D. Samples of the thus obtained formulation were then kept under various storage conditions for 3 weeks (22° C., −20° C. and cycling temperatures between −10° C. and +10° C. every 48 h). All samples remained clear and no crystalline material was formed. All samples could be easily diluted with water.

Example 5

A formulation was prepared by the method described for example 2, replacing adjuvant B by the same amount of adjuvant D. Samples of the thus obtained formulation were then kept under various storage conditions for 3 weeks (22° C., −20° C. and cycling temperatures between −10° C. and +10° C. every 48 h). All samples remained clear and no crystalline material was formed. All samples could be easily diluted with water.

Examples 6 to 9

Formulations were prepared by the method described for example 1 with the exception that the samples were heated to 60° C. for 2 h, 4 h, 6 h and 8 h, respectively. Samples of the thus obtained formulations were then kept under various storage conditions for 1 month (22° C., −20° C. and cycling temperatures between −10° C. and +10° C. every 48 h). All samples remained clear and no crystalline material was formed. All samples could be easily diluted with water.

We claim:
1. A method for producing an emulsifiable formulation of a compound of the formula I

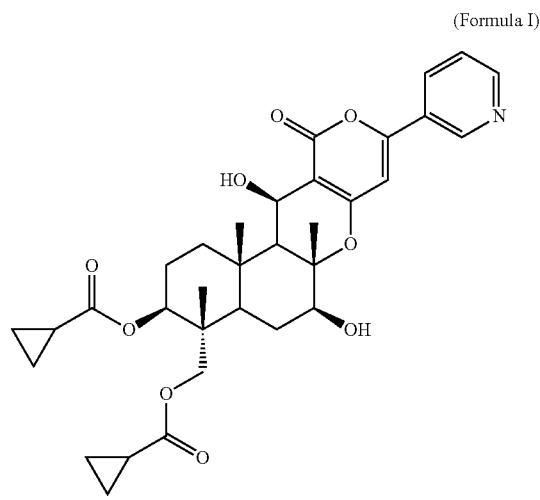

(Formula I)

comprising
a) the compound formula I;
b) an organic solvent or solvent mixture having a solubility in water of not more than 10 g/l (20° C., 1 bar) and comprising at least one aromatic hydrocarbon solvent; and
c) at least one surfactant,
wherein the surfactant comprises as component c.1) at least one non-ionic, surface active adjuvant comprising at least one component selected from the group consisting of alkoxylated aliphatic alcohols and alkoxylated polydimethylsiloxanes;
the method comprising the following steps:
i. dissolving the at least one surfactant and the compound of formula I in the organic solvent or solvent mixture to obtain a clear solution of the at least one surfactant and the compound of the formula I;
ii. heating the solution to a temperature of at least 40° C., wherein step i. further comprises the following successive steps:
i.1) dissolving the at least one surfactant in the organic solvent or solvent mixture, and
i.2) dissolving the compound of formula I in the solution obtained in step i.1).

2. The method of claim 1, wherein in step ii. the solution is heated to a temperature in the range from 40 to 90° C.

3. The method of claim 1, wherein in step ii. the solution is heated to a temperature of at least 40° C. for at least 0.5 h.

4. The method of claim 1, wherein the aromatic solvent makes up at least 50% by weight of the total amount of the organic solvent or solvent mixture in the formulation.

5. The method of claim 1, wherein the formulation comprises:
   a) 0.5 to 30% by weight, based on the total weight of the formulation, of the compound of formula I;
   b) 20 to 80% by weight, based on the total weight of the formulation, of the organic solvent or solvent mixture,
   c) 5 to 50% by weight, based on the total weight of the formulation, of the at least one surfactant.

6. The method of claim 1, wherein the non-ionic, surface active adjuvant comprises an alkoxylated aliphatic alcohol of the formula (A),

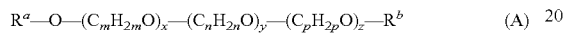   (A)

in which
R$^a$ represents C$_8$-C$_{36}$-alkyl, C$_8$-C$_{36}$-alkenyl or a mixture thereof;
R$^b$ represents H or C$_1$-C$_{12}$-alkyl;
m, n, p are different from each other and represent, independently of one another, an integer from 2 to 16;
x, y, z represent, independently of one another, a number from 0 to 50; and
x+y+z corresponds to a value from 2 to 50.

7. The method of claim 1, wherein the surfactant comprises as component c.2) at least one anionic emulsifier.

8. The method of claim 7, wherein the anionic emulsifier is selected from the group consisting of C$_1$-C$_{22}$-alkylarylsulfonates, sulfates of ethoxylated C$_4$-C$_{22}$-alkylphenols, phosphates of ethoxylated C$_4$-C$_{22}$-alkylphenols, phosphates of ethoxylated polyarylphenols and sulfates of ethoxylated polyarylphenols.

9. The method of claim 1, wherein the surfactant comprises as component c.3) at least one nonionic emulsifier, which is different from non-ionic surface active adjuvant.

10. The method of claim 7, wherein the anionic emulsifier is selected from the group consisting of C$_2$-C$_3$-polyalkoxylates of C$_{10}$-C$_{22}$-hydroxy fatty acid triglycerides, C$_2$-C$_3$-polyalkoxylates of C$_{10}$-C$_{22}$-fatty acid mono- or diglycerides, ethoxylated C$_4$-C$_{22}$-alkylphenols and ethoxylated polyarylphenols.

11. The method of claim 1, wherein the surfactant comprises as component c.4) at least one non-ionic block copolymer P comprising at least one polyethylene oxide moiety PEO and at least one polyether moiety PAO consisting of repeating units derived from C$_3$-C$_4$-alkylene oxides and/or styrene oxide, where the block copolymer P does not have alkyl or alkenyl groups with more than 6 carbon atoms.

12. The method of claim 1, wherein the formulation comprises:
   a) 1 to 10% by weight, based on the total weight of the formulation, of the compound of formula I,
   b) 30 to 70% by weight, based on the total weight of the formulation, of the organic solvent or solvent mixture,
   c.1) 10 to 40% by weight, based on the total weight of the formulation, of at least one non-ionic surface active adjuvant;
   c.2) 1 to 10% by weight, based on the total weight of the formulation, of at least one anionic emulsifier,
   c.3) 1 to 10% by weight, based on the total weight of the formulation, of at least one non-ionic emulsifier different from the non-ionic surface active adjuvant,
   c.4) optionally 0.5 to 10% by weight, based on the total weight of the formulation, at least one non-ionic block copolymer P comprising at least one polyethylene oxide moiety PEO and at least one polyether moiety PAO consisting of repeating units derived from C$_3$-C$_4$-alkylene oxides and/or styrene oxide, where the block copolymer P does not have alkyl or alkenyl groups with more than 6 carbon atoms,
   where the total amount of components a), b), c.1), c.2), c.3) and, if present, component c.4) add up to at least 90% by weight of the total amount of the formulation.

13. The method of claim 2, wherein in step ii. the solution is heated to a temperature in the range from 45 to 85° C.

14. The method of claim 1, wherein the concentration of the solution compound formula I is from >1 to 20% by weight based on the total weight of the solution.

* * * * *